(12) United States Patent
Ohara et al.

(10) Patent No.: US 6,890,421 B2
(45) Date of Patent: May 10, 2005

(54) ELECTROCHEMICAL METHODS AND DEVICES FOR USE IN THE DETERMINATION OF HEMATOCRIT CORRECTED ANALYTE CONCENTRATIONS

(75) Inventors: Timothy J. Ohara, Danville, CA (US); Mahyar Z. Kermani, Pleasanton, CA (US)

(73) Assignee: LifeScan, Inc., Milpitas, CA (US)

( * ) Notice: Subject to any disclaimer, the term of this patent is extended or adjusted under 35 U.S.C. 154(b) by 156 days.

(21) Appl. No.: 10/144,095

(22) Filed: May 10, 2002

(65) Prior Publication Data

US 2002/0125145 A1 Sep. 12, 2002

Related U.S. Application Data

(63) Continuation of application No. 09/497,304, filed on Feb. 2, 2000, now Pat. No. 6,475,372.

(51) Int. Cl.$^7$ .......................................... G01N 27/327
(52) U.S. Cl. .................... 205/777.5; 205/792

(58) Field of Search ................... 204/403.01, 403.14, 204/403.04, 403.09, 403.11, 403.12

(56) References Cited

U.S. PATENT DOCUMENTS

| 5,942,102 A | 8/1999 | Hodges et al. ............. 205/775 |
| 6,475,372 B1 * | 11/2002 | Ohara et al. ............. 205/777.5 |

FOREIGN PATENT DOCUMENTS

| EP | 0735 363 A1 | 2/1996 | ......... G01N/27/327 |
| EP | 0928 967 A2 | 7/1999 | ......... G01N/33/487 |
| EP | 1 081 490 | 3/2001 | |
| WO | 97/18465 | 5/1997 | |
| WO | WO 99/32881 | 7/1999 | ......... G01N/27/26 |
| WO | WO 99/60391 | 11/1999 | ......... G01N/27/327 |

\* cited by examiner

*Primary Examiner*—Alex Noguerola
(74) *Attorney, Agent, or Firm*—Carol M. LaSalle; Bozicevic, Field & Francis, LLP

(57) ABSTRACT

Methods and devices for determining the concentration of an analyte in a physiological sample are provided which correct for errors in the analyte concentration measurement which are due to the hematocrit of the sample.

3 Claims, 1 Drawing Sheet

ELECTROCHEMICAL METHODS AND DEVICES FOR USE IN THE DETERMINATION OF HEMATOCRIT CORRECTED ANALYTE CONCENTRATIONS

This application is a continuation of application Ser. No. 09/497,304 filed Feb. 2, 2000 and now U.S. Pat. No. 6,675,372.

FIELD OF THE INVENTION

The field of this invention is analyte determination, particularly electrochemical analyte determination and more particularly the electrochemical determination of blood analytes.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a reaction zone in an electrochemical cell comprising two electrodes, i.e. a reference and working electrode, where the electrodes have an impedance which renders them suitable for amperometric measurement. The component to be analyzed is allowed to react directly with an electrode, or directly or indirectly with a redox reagent to form an oxidisable (or reducible) substance in an amount corresponding to the concentration of the component to be analyzed, i.e. analyte. The quantity of the oxidisable (or reducible) substance present is then estimated electrochemically and related to the amount of analyte present in the initial sample.

Where the physiological sample being assayed is whole blood or a derivative thereof, the hematocrit of the sample can be a source of analytical error in the ultimate analyte concentration measurement. For example, in electrochemical measurement protocols where the analyte concentration is derived from observed time-current transients, hematocrit can slow the equilibration chemistry in the electrochemical cell and/or slow the enzyme kinetics by increasing the sample viscosity in the cell, thereby attenuating the time current response and causing analytical error.

As such, there is great interest in the development of methods of at least minimizing the hematocrit originated analytical error. In certain protocols, blood filtering membranes are employed to remove red blood cells and thereby minimize the hematocrit effect. These particular protocols are unsatisfactory in that increased sample volumes and testing times are required. Other protocols focus on the determination of the capillary fill time. However, these protocols add complexity to both the strips and devices that are used to read them. In yet other embodiments, hematocrit is separately determined using two additional electrodes, which also results in more complex and expensive strips/devices.

As such, there is continued interest in the identification of new methods for electrochemically measuring the concentration of an analyte in a physiological sample, where the method minimizes the analytical error which originates with the hematocrit of the sample.

Relevant Literature

Patent documents of interest include: U.S. Pat. No. 5,942,102 and WO 97/18465.

SUMMARY OF THE INVENTION

Methods and devices for determining the concentration of an analyte in a physiological sample are provided. In the subject methods, the physiological sample is introduced into an electrochemical cell having a working and reference electrode. A first electric potential is applied to the cell and the resultant cell current over a first period of time is measured to determine a first time-current transient. A second electric potential of opposite polarity is then applied to the cell and a second time-current transient is determined. The preliminary concentration of the analyte ($C_o$) is then calculated from the first and/or second time-current transients. This preliminary analyte concentration, less a background value, is then multiplied by a hematocrit correction factor to obtain the analyte concentration in the sample, where the hematocrit correction factor is a function of the preliminary analyte concentration and the ratio of 2 current values ($\gamma$) within the time-current transient of the electrochemical cell. The subject methods and devices are suited for use in the determination of a wide variety of analytes in a wide variety of samples, and are particularly suited for the determination of analytes in whole blood or derivatives thereof, where an analyte of particular interest is glucose.

DESCRIPTION OF THE SPECIFIC EMBODIMENTS

Figure 1:
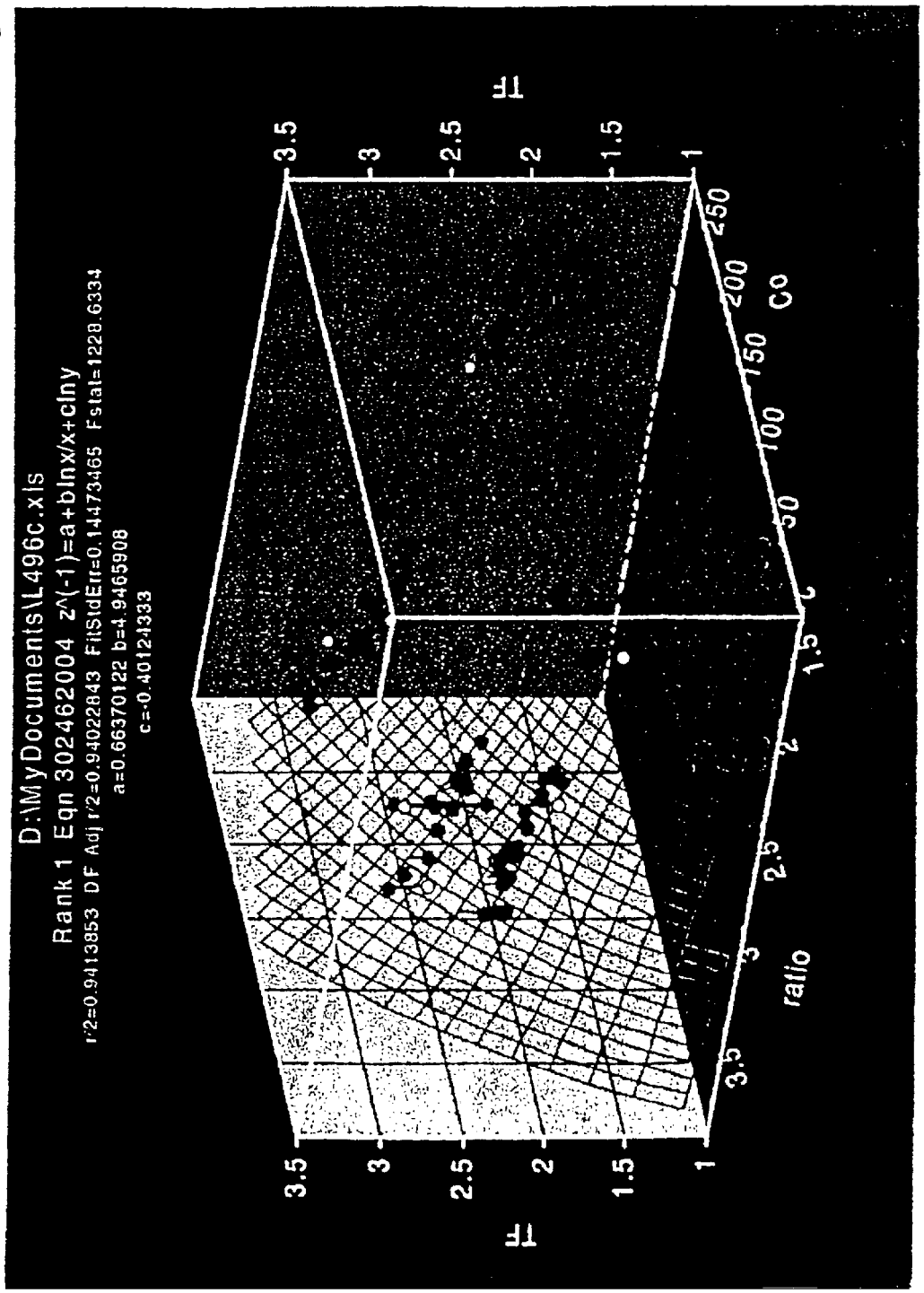
FIG. 1 provides a three-dimensional graph of $C_o$, $\gamma$ and $\alpha(C_o, \gamma)$ derived from experimental data using a wide range of glucose and hematocrit values.

Methods and devices for determining the concentration of an analyte in a physiological sample are provided. In the subject methods, the physiological sample is introduced into an electrochemical cell having a working and reference electrode. A first electric potential is applied to the cell and the resultant cell current over a first period of time is measured to determine a first time-current transient. A second electric potential of opposite polarity is then applied to the cell and a second a time-current transient is determined. The preliminary concentration of the analyte is then calculated from the first and/or second time-current transient. This preliminary analyte concentration, less a background value, is then multiplied by a hematocrit correction factor to obtain the analyte concentration in the sample, where the hematocrit correction factor is a function of the preliminary analyte concentration and the variable $\gamma$ of the electrochemical cell. The subject methods and devices are suited for use in the determination of a wide variety of analytes in a wide variety of samples, and are particularly suited for use in the determination of analytes in whole blood or derivatives thereof, where an analyte of particular interest is glucose. In further describing the subject invention, the subject methods will be described first followed by a review of a representative device for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Methods

As summarized above, the subject invention provides a method for determining a hematocrit corrected analyte concentration value in a physiological sample. By hematocrit corrected analyte concentration is meant that the analyte concentration value determined using the subject methods has been modulated or changed to remove substantially all contribution of hematocrit to the value. In other words, the concentration value that is determined using the subject methods has been modified so that any contribution to the value from the hematocrit of the sample that would be present in the value but for the practicing of the subject methods is removed. As such, the hematocrit signal is deconvoluted from the analyte signal in the subject methods, and only the analyte signal is employed in arriving at the final hematocrit corrected analyte concentration.

The first step in the subject methods is to introduce a quantity of the physiological sample of interest into an electrochemical cell that includes spaced apart working and reference electrodes and a redox reagent system. The physiological sample may vary, but in many embodiments is generally whole blood or a derivative or fraction thereof, where whole blood is of particular interest in many embodiments. The amount of physiological sample, e.g. blood, that is introduced into the reaction area of the test strip varies, but generally ranges from about 0.1 to 10 $\mu$L, usually from about 0.9 to 1.6 $\mu$L. The sample is introduced into the reaction area using any convenient protocol, where the sample may be injected into the reaction area, allowed to wick into the reaction area, and the like, as may be convenient.

While the subject methods may be used, in principle, with any type of electrochemical cell having spaced apart working and reference electrodes and a redox reagent system, in many embodiments the subject methods employ an electrochemical test strip. The electrochemical test strips employed in these embodiments of the subject invention are made up of two opposing metal electrodes separated by a thin spacer layer, where these components define a reaction area or zone in which is located a redox reagent system.

In certain embodiments of these electrochemical test strips, the working and reference electrodes are generally configured in the form of elongated rectangular strips. Typically, the length of the electrodes ranges from about 1.9 to 4.5 cm, usually from about 2.0 to 2.8 cm. The width of the electrodes ranges from about 0.38 to 0.76 cm, usually from about 0.51 to 0.67 cm. The reference electrodes typically have a thickness ranging from about 10 to 100 nm and usually from about 10 to 20 nm. In certain embodiments, the length of one of the electrodes is shorter than the length of the other electrode, typically about 0.32 cm. The shorter electrode may be the working or reference electrode.

The working and reference electrodes are further characterized in that at least the surface of the electrodes that faces the reaction area in the strip is a metal, where metals of interest include palladium, gold, platinum, silver, iridium, carbon, doped tin oxide, stainless steel and the like. In many embodiments, the metal is gold or palladium. While in principle the entire electrode may be made of the metal, each of the electrodes is generally made up of an inert support material on the surface of which is present a thin layer of the metal component of the electrode. In these more common embodiments, the thickness of the inert backing material typically ranges from about 51 to 356 $\mu$m, usually from about 102 to 153 $\mu$m while the thickness of the metal layer typically ranges from about 10 to 100 nm and usually from about 10 to 40 nm, e.g. a sputtered metal layer. Any convenient inert backing material may be employed in the subject electrodes, where typically the material is a rigid material that is capable of providing structural support to the electrode and, in turn, the electrochemical test strip as a whole. Suitable materials that may be employed as the backing substrate include plastics, e.g. PET, PETG, polyimide, polycarbonate, polystyrene, silicon, ceramic, glass, and the like.

A feature of the electrochemical test strips used in these embodiments of the subject methods is that the working and reference electrodes as described above face each other and are separated by only a short distance, such that the distance between the working and reference electrode in the reaction zone or area of the electrochemical test strip is extremely small. This minimal spacing of the working and reference electrodes in the subject test strips is a result of the presence of a thin spacer layer positioned or sandwiched between the working and reference electrodes. The thickness of this spacer layer generally should be less than or equal to 500 $\mu$m, and usually ranges from about 102 to 153 $\mu$m. The spacer layer is cut so as to provide a reaction zone or area with at least an inlet port into the reaction zone, and generally an outlet port out of the reaction zone as well. The spacer layer may have a circular reaction area cut with side inlet and outlet vents or ports, or other configurations, e.g. square, triangular, rectangular, irregular shaped reaction areas, etc. The spacer layer may be fabricated from any convenient material, where representative suitable materials include PET, PETG, polyimide, polycarbonate, and the like, where the surfaces of the spacer layer may be treated so as to be adhesive with respect to their respective electrodes and thereby maintain the structure of the electrochemical test strip. Of particular interest is the use of a die-cut double-sided adhesive strip as the spacer layer.

The electrochemical test strips used in these embodiments of the subject invention include a reaction zone or area that is defined by the working electrode, the reference electrode and the spacer layer, where these elements are described above. Specifically, the working and reference electrodes define the top and bottom of the reaction area, while the spacer layer defines the walls of the reaction area. The volume of the reaction area is at least about 0.1 $\mu$L, usually at least about 1 $\mu$L and more usually at least about 1.5 $\mu$L, where the volume may be as large as 10 $\mu$L or larger. As mentioned above, the reaction area generally includes at least an inlet port, and in many embodiments also includes an outlet port. The cross-sectional area of the inlet and outlet ports may vary as long as it is sufficiently large to provide an effective entrance or exit of fluid from the reaction area, but generally ranges from about $9 \times 10^{-4}$ to $5 \times 10^{-3}$ cm$^2$, usually from about $1.3 \times 10^{-3}$ to $2.5 \times 10^{-3}$ cm$^2$.

Present in the reaction area is a redox reagent system, which reagent system provides for the species that is measured by the electrode and therefore is used to derive the concentration of analyte in a physiological sample. The redox reagent system present in the reaction area typically includes at least an enzyme(s) and a mediator. In many embodiments, the enzyme member(s) of the redox reagent system is an enzyme or plurality of enzymes that work in concert to oxidize the analyte of interest. In other words, the enzyme component of the redox reagent system is made up of a single analyte oxidizing enzyme or a collection of two or more enzymes that work in concert to oxidize the analyte of interest. Enzymes of interest include oxidases, dehydrogenases, lipases, kinases, diphorases, quinoproteins, and the like.

The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the redox reagent system is a glucose oxidizing enzyme, e.g. a glucose oxidase or glucose dehydrogenase.

The second component of the redox reagent system is a mediator component, which is made up of one or more mediator agents. A variety of different mediator agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, and the like. In those embodiments where glucose in the analyte of interest and glucose oxidase or glucose dehydrogenase are the enzyme components, mediators of particular interest are ferricyanide, and the like.

Other reagents that may be present in the reaction area include buffering agents, e.g. citraconate, citrate, malic, maleic, phosphate, "Good" buffers and the like. Yet other agents that may be present include: divalent cations such as calcium chloride, and magnesium chloride; pyrroloquinoline quinone; types of surfactants such as Triton, Macol, Tetronic, Silwet, Zonyl, and Pluronic; stabilizing agents such as albumin, sucrose, trehalose, mannitol, and lactose.

The redox reagent system is generally present in dry form. The amounts of the various components may vary, where the amount of enzyme component typically ranges from about 1 to 100 mg/mL, usually from about 5 to 80 mg/mL; and the amount of mediator component typically ranges from about 5 to 1000 mM, usually from about 90 to 900 mM.

Following sample introduction, first and second time-current transients are obtained. The first and second time-current transients are obtained by applying a constant electric potential to the cell and observing the change in current over a period of time in the cell. In other words, first and second pulses are applied to the cell and the resultant time-current transients are observed. As such, the first time-current transient is obtained by applying a constant electric potential or first pulse to the cell, e.g. between the working and the reference electrodes, and observing the change in current over time between the electrodes, i.e. change in cell current, to obtain the first time-current transient. The magnitude of the first applied electric potential generally ranges from about 0 to −0.6 V, usually from about −0.2 to −0.4 V. The length of time over which the current between the electrodes is observed to obtain the first time-current transient typically ranges from about 3 to 20 seconds, usually from about 4 to 10 seconds.

The second time current is obtained by applying a second constant electric potential or second pulse, typically of opposite polarity from the first constant electric potential, to the electrodes and observing the change in current between the electrodes for a second period of time. The magnitude of this second constant electric potential typically ranges from about 0 to +0.6 V, usually from about +0.2 to +0.4 V, where in many embodiments the magnitude of the second electric potential is the same as the magnitude of the first electric potential. The second time period typically ranges from about 1 to 10 seconds, usually from about 2 to 4 seconds. By observing the change in current between the electrodes over this second period of time, a second time-current transient for the cell is determined.

The overall time period required to obtain the requisite first and second time-current transients, as described above, is relatively short in certain embodiments. In such embodiments, the total amount of time required to obtain the first and second time-current transients is less than about 30 seconds, usually less than about 20 seconds and more usually less than about 14 seconds.

The next step in the subject methods is to use the observed first and second time-current transients, obtained as described above, to determine: (a) the variable γ of the electrochemical cell used in the subject methods; and (b) a preliminary analyte concentration for the analyte of interest in the sample.

The variable γ employed in the subject methods is defined to describe the deviation of the electrochemical cell from ideality. By way of background, it should be noted that γ should approach unity under ideal conditions, i.e. reagent equilibration and glucose reaction are complete before the end of the first pulse. Any of these conditions not being complete will cause the ratio to deviate fron non-unity values. The numerator of γ is defined as the steady-state current observed following application of the second electric potential to the cell, i.e. predicted value at t=∞ of the second time-current transient. The denominator is defined as the average current over a short time period near the end of the first period of time, i.e. near the end of the application of the first electric potential or first pulse. The short period of time from which the average current is determined typically ranges from 0.2 to 2 seconds, usually from about 0.2 to 1.5 seconds and more usually from about 0.2 to 1.25 seconds, where in many embodiments the short period of time is about 0.3 second. The average current is determined at a time near the end of the first time period, typically within about 0.1 to 1 second. In certain embodiments, the variable γ is described by the formula:

$$\gamma = i_{ss}/i_{pp}$$

where:

$i_{ss}$ is the steady-state current of the second applied electric potential; and $i_{pp}$ is the average current over a short period of time near the end of first time period, i.e. near the end of the time during which the first electric potential is applied to the cell. For example, where the first time period is 10 seconds long, the average current may be the average current from 8.5 to 9.5 seconds of the 10 second long period, which is a 1.0 second time period 0.5 seconds from the end of the first time period As mentioned above, the first and second time-current transients are also employed to derive a preliminary analyte concentration value for the sample being assayed. In many embodiments, the preliminary analyte concentration is determined by using the following equations:

$$i(t) = i_{ss}\{1 + 4\exp(-4\pi^2 Dt/L^2)\}$$

$$i_{ss} = 2FADC_o/L$$

where $i_{ss}$ is the steady-state current following application of the second electric potential;

i is the measured current which is a function of time

D is the diffusion coefficient of the cell, where this coefficient may be determined from Fick's first law, i.e. $J(x,t) = -D {dC(x,t)}/{dx}$ L is the spacer thickness;

t is the time for the application of the $2^{nd}$ electric potential where t=0 for the beginning of the pulse $C_o$ is the preliminary concentration of the analyte;

F is faraday's constant, i.e. $9.6485 \times 10^4$ C/mol; and

A is the area of the working electrode.

Using the above equations and steps, the observed first and second time-current transients are used to determine the variable γ of the electrochemical cell employed in the subject method and the preliminary concentration value of the analyte of interest in the assayed physiological sample.

From the determined variable γ and preliminary analyte concentration value, a hematocrit correction factor is determined, which hematocrit correction factor is used to obtain a hematocrit corrected analyte concentration value from the initial or preliminary analyte concentration value described above. The hematocrit correction factor is a factor with which the preliminary analyte concentration (typically less a background value) may be multiplied in order to obtain a hematocrit corrected analyte concentration value, i.e. a concentration value from which the hematocrit component has been removed. The hematocrit correction factor is a function of both the preliminary analyte concentration value and the variable γ of the electrochemical cell.

Any hematocrit correction factor that can be multiplied by the preliminary concentration value (usually less a background value, as described in greater detail below) may be employed in the subject methods. One class of hematocrit correction factors that find use in the subject methods are those that are derived from a three dimensional graph of $C_o$, γ and α($C_o$, γ) obtained from experimental data using a wide range of analyte and hematocrit values. The hematocrit correction factor (α($C_o$, γ)) is determined using the formula:

α($C_o$, γ)=actual concentration/($C_o$-Background Value)

(For example, where the analyte is glucose, α($C_o$, γ) in many embodiments equals the glucose concentration as determined using the Yellow Springs Instrument glucose analyzer model 23A (as described in U.S. Pat. No. 5,968,760 the disclosure of which is herein incorporated by reference) divided by the $C_o$ less a background value, e.g. 22 mg/dL). This class of hematocrit correction factors are typically equations which fit a smooth surface function that minimizes the error between the predicted and actual data. See e.g. the experimental section, infra. One representative hematocrit correction factor that finds use in the subject methods is:

1/((0.6637)+((4.9466*ln($C_o$))/$C_o$)+(-0.4012*ln(γ)))

In determining the hematocrit corrected concentration of analyte according to the subject invention, the preliminary analyte concentration ($C_o$) as determined above, less a background signal value, is multiplied by the hematocrit correction factor. The background value that is subtracted from the preliminary concentration value depends on the analyte being measured. For glucose, this value typically ranges from about 0 to 40 mg/dL, usually from about 8 to 25 mg/dL, where in many embodiments the background value is about 22 mg/dL or is 22 mg/dL.

Generally, the following formula is employed to determine the hematocrit corrected analyte concentration according to the subject invention:

hematocrit corrected concentration=hematocrit correction factor× [$C_o$-β]

where

β is the background value; and $C_o$ is the preliminary analyte concentration.

The above described methods yield a hematocrit corrected analyte concentration value, i.e. a concentration value in which the hematocrit component has been deconvoluted and removed. As such, the above described methods provide for an accurate value of the concentration of the analyte in the sample being assayed.

The above computational steps of the subject method may be accomplished manually or through the use of an automated computing means, where in many embodiments the use of an automated computing means, such as is described in connection with the subject devices discussed below, is of interest.

Devices

Also provided by the subject invention are meters for use in practicing the subject invention. The subject meters are typically meters for amperometrically measuring the hematocrit corrected concentration of an analyte in a physiological sample. The subject meters typically include: (a) a means for applying a first electric potential to an electrochemical cell into which the sample has been introduced and measuring cell current as a function of time to obtain a first time-current transient; (b) a means for applying a second electric potential to the electrochemical cell and measuring cell current as a function of time to obtain a second time-current transient; (c) a means for determining a preliminary analyte concentration value and a variable γ from said first and second time-currents; and (d) a means for removing the hematocrit component from the preliminary concentration value to derive the hematocrit corrected analyte concentration in said sample. Means (a) and (b) may be any suitable means, where representative means are described in WO 97/18465 and U.S. Pat. No. 5,942,102; the disclosures of which are herein incorporated by reference. Means (c) and (d) are typically computing means present in the meter which are capable of using the measured first and second time current transients to ultimately obtain the hematocrit corrected analyte concentration. As such, means (c) is typically a means that is capable of determining the preliminary concentration of the analyte of interest and the variable γ from the first and second time-current transients using the equations described above. Likewise, means (d) is typically a means that is capable of determining the hematocrit corrected analyte concentration using the equations described above, where this means typically comprises the hematocrit correction factor.

The following examples are offered by way of illustration and not by way of limitation.

EXPERIMENTAL

I. Electrochemical Test Strip Preparation

An electrochemical test strip consisting of two metallized electrodes oriented in a sandwich configuration was prepared as follows. The top layer of the test strip was a gold sputtered Mylar strip. The middle layer was a double-sided adhesive with a punched hole that defined the reaction zone or area. The punched hole was a circle with two juxtaposed rectangular inlet and outlet channels. The bottom layer of the test strip was sputtered palladium on Mylar. A film of ferricyanide and glucose dehydrogenase PQQ was deposited on the palladium sputtered surface.

II. Generation of Experimental Data

First and second time current transients for a number of different samples varying by glucose concentration and hematocrit were obtained as follows. Sample was applied to the strip which actuated an applied potential of −0.03V for a period of 10 seconds which was then followed by a second pulse of +0.3V for a period of 3 to 10 seconds (where these electrode potentials are with respect to the gold electrode).

III. Derivation of Hematocrit Correction Factor for Glucose

For a wide range of glucose and hematocrit values measured as described above, $C_o$, the variable $\gamma$ and $\alpha(C_o, \gamma)$ were derived.

$C_o$ was derived using the equations:

$$i(t) = i_{ss}\{1 + 4\exp(-4\pi^2 Dt/L^2)\}$$

$$i_{ss} = 2FADC_o/L$$

where $i_{ss}$ is the steady-state current following application of the second electric potential;

i is the measured current which is a function of time

D is the diffusion coefficient of the cell, where this coefficient may be determined from Fick's first law, i.e. $J(x,t) = -D \frac{dC(x,t)}{dx}$ L is the spacer thickness;

t is the time for the application of the $2^{nd}$ electric potential where t=0 for the beginning of the pulse;

$C_o$ is the preliminary concentration of the analyte;

F is faraday's constant, i.e. $9.6485 \times 10^4$ C/mol; and

A is the area of the electrode surface.

The variable $\gamma$ was derived using the equation:

$$\gamma = i_{ss}/i_{pp}$$

where:

$i_{ss}$ is the steady-state current of the second applied electric potential or second pulse; and $i_{pp}$ is the average current from 8.5 to 9.5 seconds of the 10 s long period during which the first pulse was applied.

$\alpha(C_o, \gamma)$ was determined using the equation:

$$\alpha(C_o, \gamma) = YSI \text{ concentration}/(C_o - 22 \text{ mg/dL})$$

where YSI is the glucose concentration as determined using the Yellow Springs Instrument glucose analyzer model 23A (as described in U.S. Pat. No. 5,968,760 the disclosure of which is herein incorporated by reference).

A three-dimensional graph of $C_o$, $\gamma$ and $\alpha(C_o, \gamma)$ as determined above for a wide range of glucose and hematocrit values was prepared and is shown in FIG. 1. A simple equation fit was then performed on the graph to define the surface. The residual of the fitted data was monitored to ascertain the quality of the model equation. The empirical equation was found to be:

Hematocrit Correction Factor=$1/((0.6637) + ((4.9466 * ln(C_o))/C_o) + (-0.4012 * ln(\gamma)))$ The above correction factor was found to be valid for those situations where the $\gamma > 0.7$ and $C_o > 40$ mg/dL.

IV. Comparison of Hematocrit Corrected Values to YSI determined Values.

A prediction data set was generated by testing several glucose strips with a wide range of glucose and hematocrit levels. From this data a hematocrit correction equation was derived using a model which fits the terms $C_o$, $\gamma$, and $\alpha(C_o, \gamma)$. It was found that using the hematocrit correction equation on the prediction data set causes the majority of data points to fall within +/−15%. It was also found that the bias of the glucose results to 42% hematocrit, indicating that the hematocrit effect on this data set is minimal. In order to confirm this algorithm another batch of glucose sesnsors was tested with a different blood donor. It was found that the algorithm still corrects for the hematocrit effect in a manner analogous to the earlier findings.

The above results and discussion demonstrate that subject invention provides a simple and powerful tool to obtain analyte concentration values in which hematocrit derived error is substantially if not entirely eliminated. As the subject methods rely solely on the measurement of time-current transients, they may be practiced with relatively simple electrochemical devices. Furthermore, only small sample volumes need be employed and relatively quick assay times are provided. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for determining the concentration of an analyte in a physiological sample, said method comprising:
    (a) introducing said physiological sample into an electrochemical cell comprising:
        (i) spaced apart working and reference electrodes; and
        (ii) a redox reagent system comprising an enzyme and a mediator;
    (b) applying a first electric potential having a first polarity to said reaction cell and measuring cell current as a function of time to obtain a first time-current transient;
    (c) applying a second electric potential having a second polarity to said cell, wherein said second polarity is opposite said first polarity, and measuring cell current as a function of time to obtain a second time-current transient;
    (d) deriving a preliminary analyte concentration from said first and second time-current transients; and
    (e) multiplying said preliminary analyte concentration less a background value by a correction factor to derive said corrected analyte concentration in said sample;
    whereby the corrected concentration of said analyte in said sample is determined.

2. The method according to claim 1, wherein said physiological sample is whole blood or a derivative thereof.

3. The method according to claim 1, wherein said analyte is glucose.

* * * * *